United States Patent [19]

Brown et al.

[11] Patent Number: 4,663,331

[45] Date of Patent: May 5, 1987

[54] 1,2,5-THIADIAZOL-3,4-DIAMINES

[75] Inventors: Thomas H. Brown, Tewin; Peter Blurton, Welwyn Garden City, both of England

[73] Assignee: SmithKline & French Laboratories Limited, Welwyn Garden City, England

[21] Appl. No.: 819,338

[22] Filed: Jan. 16, 1986

[30] Foreign Application Priority Data

Jan. 22, 1985 [GB] United Kingdom ................ 8501535

[51] Int. Cl.$^4$ .................. A61K 31/445; C07D 403/12
[52] U.S. Cl. .................................... 514/326; 514/183; 514/212; 514/362; 546/209; 546/246; 548/135; 548/569; 540/480; 540/603; 540/450; 540/609; 564/501; 564/511
[58] Field of Search ....................... 548/135; 546/209; 540/480, 603; 514/183, 212, 326, 362

[56] References Cited

U.S. PATENT DOCUMENTS 4,374,248  2/1983  Crenshaw et al. .................. 548/135

OTHER PUBLICATIONS

Resul, B., Dahlbom, R., Ringdahl, B., and Jenden, D., Eur. J. Med. Chem.—Chim. Ther., 1982-17, No. 4, pp. 317–322.

Primary Examiner—Robert T. Bond
Attorney, Agent, or Firm—Linda E. Hall; Stuart R. Suter; Alan D. Lourie

[57] ABSTRACT

This invention relates to Mannich-alkynyl aminothiadiazole oxides having histamine $H_2$-antagonist activity. A particular compound of this invention is 3-amino-4-[7-piperidinohept-5-ynylamino]-1,2,5-thiadiazole-1-oxide.

13 Claims, No Drawings

1,2,5-THIADIAZOL-3,4-DIAMINES

The present invention relates to alkyne derivatives and in particular to such compounds substituted by a Mannich group. This invention further relates to pharmaceutical compositions containing these compounds and to a method of blocking histamine H2-receptors by administering them.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427 (1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

Accordingly the present invention provides the compounds of the formula (I):

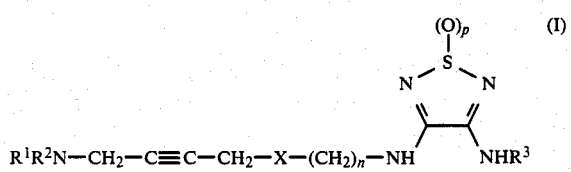

and pharmaceutically acceptable salts thereof,
wherein
$R^1$ and $R^2$ are independently hydrogen or $C_{1-6}$alkyl, or $R^1$ and $R^2$ together represent $-(CH_2)_q-$ wherein q is 4 to 7, to form together with the nitrogen atom to which they are attached, a 5–8 membered saturated ring, optionally substituted by $C_{1-6}$alkyl;
X is $-CH_2-$ or sulphur;
n is 2 or 3, or if X is $-CH_2-$ n can also be 1;
p is 1 or 2; and
$R^3$ is hydrogen, $C_{1-6}$alkyl, $C_{3-6}$alkenyl or $C_{3-6}$alkynyl (wherein the unsaturated bond is not adjacent to the $-NH-$ moiety).

Suitably $R^1$ is $C_{1-6}$alkyl for example methyl or ethyl.
Suitably $R^2$ is $C_{1-6}$alkyl for example methyl or ethyl.
Preferably $R^1$ and $R^2$ have the same value, for example they are both methyl. In another aspect $R^1$ and $R^2$ together with the nitrogen atom to which they are attached form a pyrrolidino, piperidino or hexahydroazepino ring.

Suitably X is sulphur. Preferably X is $-CH_2-$.
Suitably $-CH_2X(CH_2)_n-$ is methylthioethyl, trimethylene, tetramethylene or pentamethylene. Preferably $-CH_2X(CH_2)_n-$ is trimethylene.
Preferably p is 2.
$R^3$ is hydrogen, $C_{1-6}$alkyl for example methyl, ethyl or propyl, $C_{3-6}$alkenyl for example allyl, or $C_{3-6}$alkynyl for example propargyl. Preferably $R^3$ is hydrogen, methyl or ethyl and in particular $R^3$ is hydrogen.

Particular compounds of this invention are:
3-amino-4-[7-piperidinohept-5-ynylamino]-1,2,5-thiadiazole-1-oxide,
3-amino-4-[7-dimethylaminohept-5-ynylamino]-1,2,5-thiadiazole-1-oxide,
3-amino-4-[7-dimethylaminohept-5-ynylamino]-1,2,5-thiadiazole-1,1-dioxide, and
3-amino-4-[6-dimethylaminohex-4-ynylamino]-1,2,5-thiadiazole-1,1-dioxide.

Suitable pharmaceutically acceptable acid addition salts of the compounds of the formula (I) include those formed with hydrochloride, hydrobromic, sulphuric phosphoric, acetic, citric, maleic, lactic, ascorbic, fumaric, oxalic, methanesulphonic and ethanesulphonic acids.

The activity of the compounds of the formula (I) as histamine $H_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

The measurement of inhibition of histamine-stimulated secretion of gastric acid from the lumen-perfused stomachs of rats anaesthetised with urethane, and the measurement of inhibition of histamine-induced tachycardia in the isolated guinea pig right atrium, are detailed in U.S. Pat. No. 4,385,058.

In order to use the compounds of the formula (I) or pharmaceutically acceptable salts thereof for medical purposes, they are normally formulated in accordance with standard pharmaceutical practice as pharmaceutical compositions.

The invention further provides pharmaceutical compositions comprising a compound of the formula (I) or a pharmaceutically acceptable salt thereof together with a pharmaceutically acceptable carrier.

The compounds of the formula (I) and pharmaceutically acceptable salts thereof may be administered orally, parenterally, cutaneously or rectally.

The compounds of the formula (I) and pharmaceutically acceptable salts thereof which are active when given orally can be formulated as syrups, tablets, capsules and lozenges. A syrup formulation will generally consist of a suspension or solution of the compound or salt in a suitable liquid carrier for example, ethanol, glycerine or water with a flavouring or colouring agent. Where the composition is in the form of a tablet any suitable pharmaceutical carrier routinely used for prearing solid formulations may be used. Examples of such carriers include magnesium stearate, starch, lactose, sucrose and cellulose.

Typical parenteral compositions consist of a solution or suspension of the compound or pharmaceutically acceptable salt thereof in a sterile aqueous carrier or parenterally acceptable oil.

Typical compositions for administration to the skin include lotions and creams in which the compound of the formula (I) or pharmaceutically acceptable salt thereof is contained in a liquid vehicle.

A typical suppository formulation comprises a compound of the formula (I) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably 0.5 to 25 mg) of a compound of the formula (I) or a pharmaceutically acceptable salt thereof calculated as the free base.

The invention also provides a method of blocking histamine $H_2$-receptors which comprises administering to an animal an effective amount to block said receptors of a compound of the formula (I) or pharmaceutically acceptable salt thereof.

The compounds of this invention will normally be administered to a subject for the treatment of peptic ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonists. Thus an adult patient will receive an oral dose of between 15 mg and 1500 mg, preferably between 15 mg and 250 mg, or an intravenous, subcutaneous, or intramuscular dose of between 0.5 mg and 150 mg, preferably between 1.0 mg and 20 mg, of a compound of the formula (I) or pharmaceutically acceptable salt thereof calculated as the free base, the composition being administered 1 to 6 times per day, suitably 1 to 4 times a day.

Processes for preparing the compounds of the formula (I) and pharmaceutically acceptable salts thereof comprise:

(a) reacting a compound of the formula (II):

$$HC{\equiv}C-CH_2-X-(CH_2)_n-NH\underset{\underset{Q}{\diagup\diagdown}}{\overset{(O)_p}{\underset{\|}{N{\diagdown}\overset{S}{\underset{}{}}{\diagup}N}}}NHR^3 \quad (II)$$

wherein n, X, p and $R^3$ are as hereinbefore defined, with a Mannich reagent in the presence of a catalyst; or (b) reacting a compound of the formula (III) with a compound of the formula (IV):

$$R^1R^2N-CH_2-C{\equiv}C-CH_2-X-(CH_2)_n-NH_2 \quad (III)$$

$$\underset{Q}{\diagup}\overset{(O)_p}{\underset{\|}{N{\diagdown}\overset{S}{\underset{}{}}{\diagup}N}}\underset{NHR^3}{\diagdown} \quad (IV)$$

wherein $R^1$, $R^2$, $R^3$, p, X and n are as hereinbefore defined and Q is a group displaceable by amine; or (c) reacting a compound of the formula (V) with an amine $R^3NH_2$:

$$R^1R^2N-CH_2-C{\equiv}C-CH_2-X-(CH_2)_n-NH\underset{\underset{}{\diagup\diagdown}L}{\overset{(O)_p}{\underset{\|}{N{\diagdown}\overset{S}{\underset{}{}}{\diagup}N}}} \quad (V)$$

wherein $R^1$, $R^2$, $R^3$, n, X and p are hereinbefore defined and L is a group displaceable by amine;

(d) for preparing compounds wherein X is sulphur, reacting a compound of the formula (VI) or a chemical equivalent thereof with a compound of the formula (VII):

$$R^1R^2NCH_2-C{\equiv}C-CH_2-SH \quad (VI)$$

$$L^1(CH_2)_nNH\underset{\underset{}{\diagup\diagdown}NHR^3}{\overset{(O)_p}{\underset{\|}{N{\diagdown}\overset{S}{\underset{}{}}{\diagup}N}}} \quad (VII)$$

wherein $R^1$, $R^2$, n, p and $R^3$ are as hereinbefore defined and $L^1$ is a group displaceable by thiol or chemical equivalent thereof;

(e) for preparing compounds wherein X is sulphur, reacting a compound of the formula (VIII) with a compound of the formula (IX) or chemical equivalent thereof:

$$R^1R^2NCH_2-C{\equiv}C-CH_2-L^2 \quad (VIII)$$

$$HS(CH_2)_nNH\underset{\underset{}{\diagup\diagdown}NHR^3}{\overset{(O)_p}{\underset{\|}{N{\diagdown}\overset{S}{\underset{}{}}{\diagup}N}}} \quad (IX)$$

wherein $R^1$, $R^2$, n, p and $R^3$ are as hereinbefore defined and $L^2$ is a group displaceable by thiol or chemical equivalent thereof;

(f) for preparing compounds wherein X is $-CH_2-$, reacting a compound of the formula (X) with a compound of the formula (XI):

$$R^1R^2NCH_2C{\equiv}CH \quad (X)$$

-continued

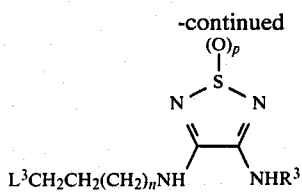
(XI)

wherein $R^1$, $R^2$, n, p and $R^3$ are as hereinbefore defined and $L^3$ is a leaving group, in the presence of a base; and thereafter optionally forming a pharmaceutically acceptable salt.

In the reaction of a compound of the formula (II) with a Mannich reagent, suitable reagents include formaldehyde together with an amine $R^1R^2NH$ or salt thereof. This reaction may be carried out by treating an amine salt with aqueous formaldehyde and a compound of the formula (II), or by refluxing an amine salt with paraformaldehyde and a compound of the formula (II) in a convenient solvent such as ethanol. Alternatively where $R^1$ and $R^2$ are each $C_{1-4}$alkyl, the Mannich reagent may be a di-($C_{1-4}$alkyl) methylene ammonium salt for example dimethylmethylene ammonium chloride or iodide, or may be a bis di-$C_{1-4}$alkylaminomethane, for example bis(dimethylamino)methane. The reaction is performed in the presence of a catalyst, generally an ion such as cupric, cuprous, ferric, ferrous, argentic or argentous. One source of cupric ion, which need only be present in catalytic quantities, is cupric chloride. One source of cuprous ion, which need only be present in catalytic quantities, is cuprous chloride. Alternatively catalytic amounts of cupric sulphate or cupric acetate may be used. A convenient source of ferric ion is ferric chloride.

In the reaction of the compounds of the formulae (III) and (IV), conveniently Q is a leaving group such as halo, optionally substituted phenylthio, $C_{1-6}$alkoxy or $C_{1-6}$alkylthio. Suitably the reaction is performed in an inert organic solvent for example a $C_{1-4}$alkanol, in particular methanol, and can be performed at any non-extreme temperature.

In the reaction of the compounds of the formulae (V) and an amine $R^3NH_2$ conveniently L is a leaving group such as halo, optionally substituted phenylthio, $C_{1-6}$alkoxy or $C_{1-6}$alkylthio. Suitably the reaction is performed in an inert organic solvent for example a $C_{1-4}$alkanol, in particular methanol, and can be performed at any non-extreme temperature.

Suitably in the reaction between the compounds of the formulae (VI) and (VII) $L^1$ is chloro, bromo, arylsulphonyloxy for example 4-methylbenzenesulphonyloxy or $C_{1-6}$alkanesulphonyloxy for example methanesulphonyloxy. Such reactions are generally performed in the presence of a base for example triethylamine, an alkoxide or a hydroxide.

Suitably in the reaction between the compounds of the formulae (VIII) and (IX) $L^2$ is chloro, bromo, $C_{1-6}$alkanoyloxy for example acetoxy, arylsulphonyloxy for example 4-methylbenzenesulphonyloxy or $C_{1-6}$alkanesulphonyloxy for example methanesulphonyloxy. When $L^2$ is chloro or bromo it is preferable to perform the reaction in the presence of a strong base for example sodium ethoxide in ethanol. When $L^2$ is an arylsulphonyloxy or alkanesulphonyloxy group the reaction is preferably performed under mildly basic conditions for example in pyridine solution.

The reaction between the compounds of the formulae (X) and (XI) is conveniently performed under basic conditions such as using sodium in liquid ammonia. Suitably $L^3$ is halo for example bromo.

The compounds of the formula (II) can be prepared in a manner analogous to that for the preparation of compounds of the formula (I).

The compounds of the formula (III) wherein X is —$CH_2$— can be prepared by reacting a compound of the formula (XII) with a compound of the formula (XIII) wherein the amino function is protected, if necessary, for example when n is 2. Such protection can be for example as a phthalimido group:

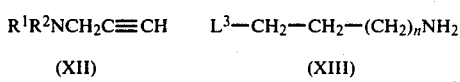

wherein $R^1$, $R^2$ and n are as hereinbefore defined and $L^3$ is a leaving group, for example halo such as bromo, under basic conditions for example sodium in liquid ammonia.

In an alternative the compounds of the formula (III) may be prepared by reacting a Mannich reagent and a compound of the formula (XIV):

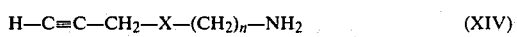

wherein n and X are as hereinbefore defined and the amino function ($NH_2$) is protected, for example as a phthalimido group. Suitably the reaction is performed in a manner similar to that described for reacting compounds of the formula (II).

In a further alternative the compounds of the formula (III) can be prepared from compounds of the formula (XV):

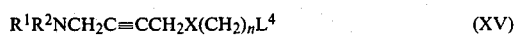

wherein $R^1$, $R^2$, X and n are as hereinbefore defined and $L^4$ is a group displaceable by amine or a group convertible thereto, for example $L^4$ may be displaced by phthalimide which group is then converted to amino. Suitably $L^4$ is a halo atom such as bromo or chloro. The compounds of the formula (XV) can, for example, be prepared by reacting a Mannich reagent with a compound: $HC\equiv CCH_2X(CH_2)_nL^4$.

An alternative method of preparing the compounds of the formula (III) wherein X is sulphur and n is 2 comprises reacting cysteamine and a compound of the formula (XVI):

wherein $R^1$, $R^2$ and $L^2$ are as hereinbefore defined, under basic conditions for example in the presence of an alkali metal alkoxide such as sodium ethoxide in an alkanol. Suitably $L^2$ is chloro or bromo in the compounds of the formula (XVI).

The compounds of the formula (V) can be prepared by reacting a compound of the formula (III) with a compound of the formula (XVII):

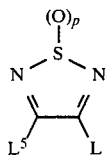

(XVII)

wherein L and p are hereinbefore defined and $L^5$ is a group displaceable by amine. Conveniently $L^5$ is selected from the values of L given hereinbefore. In a suitable aspect $L^5$ and L are the same, for example they are both methoxy. In a further suitable aspect the compound of the formula (V) is not isolated but reacted in situ to afford the compound of the formula (I).

The compounds of the formulae (XVII) and (IV) are known or preparable by known methods, see for example, U.S. Pat. No. 4,374,248 and J. Org. Chem., 40, p2743 (1975).

The compounds of the formulae (VII), (IX) and (XI) are preparable in a manner similar to that for the preparation of compounds of the formula (I). Most conveniently the compounds of the formulae (VII) and (XI) are preparable by reacting an appropriate hydroxyalkylamine with a compound of the formula (IV) and subsequently converting the hydroxy group to a group $L^1$ or $L^3$.

The following Descriptions, Examples and biological data serve to illustrate this invention.

DESCRIPTION 1

7-(Piperidino)hept-5-ynylamine (i) A flask fitted with a carbon dioxide condenser was charged with liquid ammonia (800 ml) and a few crystals of ferric nitrate. Sodium (22 g) was added over 15 minutes. Acetylene was passed through the mixture at a rate of 1 liter min$^{-1}$ for 1 hour. Then 1-bromo-4-chlorobutane (145 g) was added dropwise over 2 hours, the reaction mixture was stirred under reflux for 7 hours and allowed to stand overnight. Water was added and the product extracted into diethyl ether (5×300 ml). The organic extracts were combined, washed with dilute acid (200 ml), dried and the ether was distilled to afford an oil which was purified by distillation to give 1-chloro-5-hexyne (64.1 g), b.p. 140°–6° C.

(ii) To potassium phthalimide (37.5 g) in dimethylformamide (400 ml) at 100° C,. was added dropwise 1-chloro-5-hexyne (23.67 g) in dimethylformamide (100 ml). The reaction mixture was stirred at 100° C. for a further hour, cooled and stirred at room temperature overnight. The mixture was poured on to ice/water to give an oil, which on trituration gave as a white solid N-5-hexynyl phthalimide (18.35 g), m.p. 74°–6° C. (recrystallisation from ethanol).

(iii) N-5-Hexynyl phthalimide (7.0 g), piperidine (2.89 g), paraformaldehyde (1.14 g) and cuprous chloride (0.2 g) were stirred under reflux in dioxan (20 ml; peroxide-free) for 2 hours. The mixture was cooled, poured into water (100 ml), acidified with 5N hydrochloric acid, washed with diethyl ether (2×50 ml), basified (sodium carbonate solution) and extracted into chloroform (6×50 ml). The chloroform extracts were combined, dried and evaporated under reduced pressure to give 7-(piperidino)hept-5-ynyl-1-phthalimide (10.0 g) as a yellow oil.

(iv) 7-(Piperidino)hept-5-ynyl-1-phthalimide (10.0 g) and hydrazine hydrate (1.54 g) in ethanol (50 ml) were stirred under reflux for 6 hours (additional hydrazine hydrate (0.3 g) added after 4 hours). The mixture was allowed to stand for 5 days at room temperature, acidified with concentrated hydrochloric acid and filtered. The filtrate was evaporated under reduced pressure (azeotroped with n-propanol) to give 7-(piperidino)-hept-5-ynylamine as a yellow oil. This was treated with ethanolic HCl to give the dihydrochloride (5.4 g), m.p. 153°–5° C.

DESCRIPTION 2

7-(Dimethylamino)hept-5-ynylamine

In a manner similar to Description 1 (iii) and (iv) reaction of N-5-hexynylphthalimide, paraformaldehyde and dimethylamine, followed by treatment with hydrazine hydrate gave the title compound b.p. 110°–20° C. (0.3 mm Hg).

DESCRIPTION 3

6-(Dimethylamino)hex-4-ynylamine

In a manner similar to Description 1 (i)–(iv) 1-bromo-3-chloropropane gave 5-chloropent-1-yne which was reacted to give sequentially, N-5-phthalimidopent-1-yne, 6-(dimethylamino)hex-4-ynylphthalimide, and finally the title compound b.p. 110–125 (0.03 mm Hg).

DESCRIPTION 4

6-Dimethylaminohex-4-ynylamine

A flask fitted with a dry ice condenser was charged with liquid ammonia (250 ml). To this was added sodium (0.24 mol) in portions together with a few grains of ferric nitrate; subsequently dimethylaminoprop-2-yne (0.24 mol) was added. The reaction mixture was stirred for one hour, 3-bromopropylamine hydrochloride (0.24 mol) was added in portions and the mixture stirred for a further two hours. Anhydrous diethyl ether (150 ml) was added and excess ammonia was allowed to evaporate overnight. The reaction mixture wws dissolved in methanol and evaporated under reduced pressure to afford a residue, which was partitioned between chloroform and water. The aqueous layer was washed with chloroform (5×150 ml). The chloroform extracts were combined, dried over MgSO$_4$, filtered and evaporated under reduced pressure to give 6-dimethylaminohex-4-ynylamine as an oil (5.4 g).

DESCRIPTION 5

2-(4-Dimethylaminobut-2-ynylthio)ethylamine

Sodium (0.264 mol) was added in portions to ethanol (100 ml). When dissolution had occurred, the mixture was cooled to 0° C. and cysteamine hydrochloride (0.088 mol) was added with stirring. When all of the cysteamine had dissolved, 4-dimethylamino-1-chloro-2-butyne hydrochloride (0.088 mol) in ethanol (100 ml) was added dropwise with stirring whilst maintaining the temperature of the reaction mixture below 10° C. The reaction mixture was allowed to warm to room temperature overnight and evaporated under reduced pressure to afford an oil. This oil was taken up in aqueous solution (pH3), taken to pH8 with sodium bicarbonate and extracted with ethyl acetate. The aqueous layer was taken to pH12 and extracted with ethyl acetate. The combined ethyl acetate extracts were dried (MgSO$_4$), filtered and evaporated to afford slightly impure 2-(4-dimethylamino-but-2-ynylthio)ethylamine as a reddish-brown oil (6.63 g).

DESCRIPTION 6

2-(Prop-2-ynylthio)ethylamine hydrochloride

To the solution of sodium ethoxide prepared by the addition of sodium (3.35 g, 0.1455M) to absolute ethanol (150 ml) was added a solution of cysteamine hydrochloride (8.4 g, 0.074M) in absolute ethanol (100 ml). The resultant solution was filtered and added dropwise to a solution of propargyl bromide (8.66 g, 0.0727M) in absolute ethanol (100 ml). After addition was complete the reaction was allowed to stir at room temperature for 2 hours and then poured on to water (500 ml) plus sufficient concentrated hydrochloric acid to keep the solution acidic (approximately 10 ml). The acidic solution was extracted with ether, the aqueous phase basified with 2N sodium hydroxide to pH11 and re-extracted with ether and then ethyl acetate. The organic phases were combined, dried and evaporated to dryness to give a yellow oil (5.4 g).

This was converted to the hydrochloride salt by dissolution in ethanol/ether (1:1) and addition of ethanolic HCl. Cooling gave crystals of 2-(prop-2-ynylthio)ethylamine hydrochloride (5.4 g), m.p. 113°–115° C.

EXAMPLE 1

3-Amino-4-[7-piperidinohept-5-ynylamino]-1,2,5-thiadiazole-1-oxide

A solution of 3,4-dimethoxy-1,2,5-thiadiazole-1-oxide (2.0 g) in methanol (100 ml) was cooled to 0° C. 7-(Piperidino)hept-5-ynylamine (2.5 g) in methanol (50 ml) was added dropwise with stirring over 30 minutes maintaining the reaction temprature at 0° C. The reaction mixture was stirred at 0° C. for a further 2 hours to give a solution of 3-methoxy-4-[7-(piperidino)hept-5-ynylamino]-1,2,5-thiadiazole-1-oxide. Ammonia gas was bubbled through this solution for 30 minutes and the mixture allowed to stand for 16 hours. The reaction mixture was evaporated under reduced pressure to give an oil which was taken up in ethyl acetate, triturated and cooled to give the title compound (3.0 g), m.p. 134°–6° C. (recrystallisation from isopropanol-ethyl acetate).

EXAMPLE 2

3-Amino-4-[7-dimethylaminohept-5-ynylamino]-1,2,5-thiadiazole-1-oxide

In a similar manner to Example 1, 3,4-dimethoxy-1,2,5-thiadiazole-1-oxide (1.57 g) and 7-(dimethylamino)hept-5-ynylamine (1.5 g) were reacted to give a solution of 3-methoxy-4-[7-dimethylaminohept-5-ynylamino]-1,2,5-thiadiazole-1-oxide. Reaction with ammonia gas and purification as in Example 1 gave the title compound (1.8 g), m.p. 154°–5° C. (recrystallisation from isopropanolethyl acetate).

EXAMPLE 3

3-Amino-4-[7-dimethylaminohept-5-ynylamino]-1,2,5-thiadiazole-1,1-dioxide

In a similar manner to Example 1, 3,4-dimethoxy-1,2,5-thiadiazole-1,1-dioxide (1.07 g) and 7-(dimetylamino)hept-5-ynylamine (0.92 g) were reacted to give a solution of 3-methoxy-4-[7-dimethylaminohept-5-ynylamino]-1,2,5-thiadiazole-1,1-dioxide. Reaction with ammonia gas and purification as in Example 1 gave the title compound (1.08 g), m.p. 172°–4° C. (recrystallisation from acetonitrile).

EXAMPLE 4

3-Amino-4-[6-dimethylaminohex-4-ynylamino]-1,2,5-thiadiazole-1,1-dioxide

In a similar manner to Example 1, 3,4-dimethoxy-1,2,5-thiadiazole-1,1-dioxide (1.0 g) and 6-(dimethylamino)hex-4-ynylamine (0.79 g) were reacted to give a solution of 3-methoxy-4-[6-dimethylaminohex-4-ynylamino]-1,2,5-thiadiazole-1,1-dioxide. Reaction with ammonia and purification as in Example 1 gave the title compound (0.62 g), m.p. 183°–5° C. (recrystallisation from acetonitrile).

EXAMPLE 5

3-Amino-4-[7-piperidinohept-5-ynylamino]-1,2,5-thiadiazole-1,1-dioxide

In a manner similar to Example 1, reaction of 7-piperidinohept-5-ynylamine and 3,4-dimethoxy-1,2,5-thiadiazole-1,1-dioxide followed by reaction with ammonia gives the title compound.

EXAMPLE 6

3-Amino-4-[2-(4-dimethylaminobut-2-ynylthio)ethylamino]-1,2,5-thiadiazole-1,1-dioxide In a manner similar to Example 1, reaction of 2-(4-dimethylamino-but-2-ynylthio)ethylamine and 3,4-dimethoxy-1,2,5-thiadiazole-1,1-dioxide followed by reaction with ammonia gives the title compound.

EXAMPLE 7

3-Amino-4-[7-pyrrolidinohept-5-ynylamino]-1,2,5-thiadiazole-1-oxide (i) In a manner similar to Description 1 (iii) and (iv), reaction of N-5-hexynylphthalimide, paraformaldehyde and pyrrolidine, followed by treatment with hydrazine hydrate gives 7-pyrrolidinohept-5-ynylamine.

(ii) In a manner similar to Example 1, reaction of 7-pyrrolidinohept-5-ynylamine and 3,4-dimethoxy-1,2,5-thiadiazole-1-oxide followed by treatment with ammonia gives the title compound.

EXAMPLE 8

3-Amino-4-[7-hexahydroazepinohept-5-ynyl]-1,2,5-thiadiazole-1-oxide (i) In a manner similar to Description 1 (iii) and (iv), reaction of N-5-hexynylphthalimide, paraformaldehyde and hexahydroazepine, followed by treatment with hydrazine hydrate gives 7-hexahydroazepinohept-5-ynylamine.

(ii) In a manner similar to Example 1, reaction of 7-hexahydroazepinohept-5-ynylamine and 3,4-dimethoxy-1,2,5-thiadiazole-1-oxide followed by treatment with ammonia gives the title compound.

EXAMPLE 9

3-Methylamino-4-[6-dimethylaminohex-4-ynylamino]-1,2,5-thiadiazole-1,1-dioxide In a manner similar to Example 1, reaction of 6-dimethylaminohex-4-ynylamine and 3,4-dimethoxy-1,2,5-thiadiazole-1,1-dioxide followed by treatment with methylamine gives the title compound.

EXAMPLE 10

3-Allylamino-4-[6-dimethylaminohex-4-ynylamino]-1,2,5-thiadiazole-1,1-dioxide

In a manner similar to Example 1, reaction of 6-dimethylaminohex-4-ynylamine and 3,4-dimethoxy-1,2,5-thiadiazole-1,1-dioxide followed by treatment with allylamine gives the title compound.

EXAMPLE 11

3-Propargylamino-4-[6-dimethylaminohex-4-ynylamino]-1,2,5-thiadiazole-1,1-dioxide In a manner similar to Example 1, reaction of 6-dimethylaminohex-4-ynylamine and 3,4-dimethoxy-1,2,5-thiadiazole-1,1-dioxide followed by treatment with propargylamine gives the title compound.

EXAMPLE 12

A pharmaceutical composition for oral administration is prepared containing:

|   |   | % by weight |
|---|---|---|
| A | 3-amino-4-[7-piperidinohept-5-ynylamino]-1,2,5-thiadiazole-1-oxide | 55 |
|   | Dibasic calcium phosphate dihydrate | 20 |
|   | Approved colouring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

Other compounds of the invention, for example those specifically described in Examples 2 to 4 can be formulated into pharmaceutical compositions by a similar procedure.

To illustrate the level of activity of these compounds the following data were obtained in the standard guinea pig atrium test and the standard lumen-perfused rat test (for example see EP-A-49173).

| Compound of Example | pA$_2$ (guinea-pig atrium) | ED$_{50}$ (lumen-perfused rat) mg/kg |
|---|---|---|
| 1 | 5.52 (0.95)* | 1.1 |
| 2 | 6.19 (0.61) | 0.16 |
| 3 | 6.82 (0.50) | 0.1 |
| 4 | 7.0 (0.88) | 0.027 |

*the figures in brackets give the slope of response

What is claimed is:

1. A compound of the formula (I):

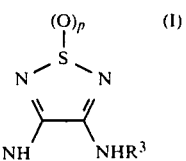

or a pharmaceutically acceptable salt thereof, wherein $R^1$ and $R^2$ are independently hydrogen or $C_{1-6}$alkyl, or $R^1$ and $R^2$ together represent —(CH$_2$)$_q$— wherein q is 4 to 7, to form together with the nitrogen atom to which they are attached, a 5–8 membered saturated ring, optionally substituted by $C_{1-6}$alkyl;

X is —CH$_2$— or sulphur;

n is 2 or 3, or if X is —CH$_2$— n can also be 1;

p is 1 or 2; and $R^3$ is hydrogen, $C_{1-6}$alkyl, $C_{3-6}$alkenyl or $C_{3-6}$alkynyl (wherein the unsaturated bond is not adjacent to the —NH— moiety).

2. A compound according to claim 1 wherein $R^1$ and $R^2$ are both $C_{1-6}$alkyl.

3. A compound according to claim 2 wherein $R^1$ and $R^2$ are both methyl.

4. A compound according to claim 1 wherein p is 2.

5. A compound according to claim 1 wherein X is —CH$_2$—.

6. A compound according to claim 1 wherein —CH$_2$X(CH$_2$)$_n$13 is trimethylene.

7. A compound according to claim 1 wherein $R^3$ is hydrogen.

8. A compound according to claim 1 which is: 3-amino-4-[7-piperidinohept-5-ynylamino]-1,2,5-thiadiazole-1-oxide or a pharmaceutically acceptable salt thereof.

9. A compound according to claim 1 which is: 3-amino-4-[7-dimethylaminohept-5-ynylamino]-1,2,5-thiadiazole-1-oxide or a pharmaceutically acceptable salt thereof.

10. A compound according to claim 1 which is: 3-amino-4-[7-dimethylaminohept-5-ynylamino]-1,2,5-thiadiazole-1,1-dioxide or a pharmaceutically acceptable salt thereof.

11. A compound according to claim 1 which is: 3-amino-4-[6-dimethylaminohex-4-ynylamino]-1,2,5-thiadiazole-1,1-dioxide or a pharmaceutically acceptable salt thereof.

12. A pharmaceutical composition having histamine H$_2$-antagonist activity which comprises a compound according to claim 1 and a pharmaceutically acceptable carrier.

13. A method of blocking histamine H$_2$-receptors which comprises administering to an animal in need thereof an effective amount to block said receptors of a compound according to claim 1.

* * * * *

UNITED STATES PATENT AND TRADEMARK OFFICE
CERTIFICATE OF CORRECTION

PATENT NO. : 4,663,331
DATED : May 5, 1987
INVENTOR(S) : Thomas H. Brown and Peter Blurton It is certified that error appears in the above-identified patent and that said Letters Patent is hereby corrected as shown below:

Col. 12, line 31, "$-CH_2X(CH_2)_n13$" should read -- $-CH_2X(CH_2)_n-$ -- .

Signed and Sealed this

Fifteenth Day of March, 1988

Attest:

DONALD J. QUIGG

Attesting Officer

Commissioner of Patents and Trademarks